(12) United States Patent
Amin et al.

(10) Patent No.: US 6,518,270 B1
(45) Date of Patent: Feb. 11, 2003

(54) HETEROCYCLIC COMPOUNDS FOR INHIBITION OF GASTRIC ACID SECRETION, PROCESSES FOR THEIR PREPARATION AND PHARMACEUTICAL COMPOSITIONS THEREOF

(75) Inventors: Kosrat Amin, Mölndal (SE); Mikael Dahlström, Mölndal (SE); Peter Nordberg, Sävedalen (SE); Ingemar Starke, Göeborg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/194,823

(22) PCT Filed: Nov. 18, 1998

(86) PCT No.: PCT/SE98/02091
§ 371 (c)(1),
(2), (4) Date: Feb. 8, 2000

(87) PCT Pub. No.: WO99/28322
PCT Pub. Date: Jun. 10, 1999

(30) Foreign Application Priority Data
Nov. 28, 1997 (SE) ................................. 9704404

(51) Int. Cl.[7] .................. A61K 31/44; A61K 31/495; C07D 471/04; C07D 487/04
(52) U.S. Cl. ............. 514/248; 514/249; 514/558; 514/300; 544/236; 544/281; 544/349; 544/350; 546/113
(58) Field of Search ................. 544/236, 281, 544/349, 350; 546/113; 514/248, 249, 258, 300

(56) References Cited

U.S. PATENT DOCUMENTS

| | | | |
|---|---|---|---|
| 4,507,294 A | 3/1985 | Bristol et al. | 514/249 |
| 5,041,442 A | 8/1991 | Romero et al. | 514/249 |

FOREIGN PATENT DOCUMENTS

| | | |
|---|---|---|
| EP | 0068378 | 1/1983 |
| EP | 0204285 | 12/1986 |
| WO | 9206979 | 4/1992 |
| WO | 9308190 | 4/1993 |
| WO | 9117164 | 11/1994 |
| WO | 9519980 | 7/1995 |
| WO | 9747603 | 12/1997 |
| WO | 9837080 | 8/1998 |
| WO | 9928322 | 6/1999 |

OTHER PUBLICATIONS

Ueda et al., Chemical Abstracts, vol. 106:138443, 1987.*
Grundler et al., Chemical Abstracts, vol. 119:180803, 1993.*
Grundler et al., Chemical Abstracts, vol. 117:111632, 1992.*
G. Sachs and J. M. Shin, The Pharmacology of the Gastric Pump: The $H^+,K^+$ ATPace[1,2], Annu. Rev. Pharmacol. Toxicol. 1995, 35:277–305.

* cited by examiner

Primary Examiner—Richard L. Raymond
(74) Attorney, Agent, or Firm—White & Case LLP

(57) ABSTRACT

The present invention relates to heterocyclic compounds of the formula (I), in which the phenyl moiety is substituted with lower alkyl in 2- and 6-position, which inhibit exogenously or endogenously stimulated gastric acid secretion and thus can be used in the prevention and treatment of gastrointestinal inflammatory diseases.

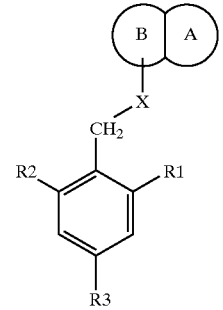

19 Claims, No Drawings

HETEROCYCLIC COMPOUNDS FOR INHIBITION OF GASTRIC ACID SECRETION, PROCESSES FOR THEIR PREPARATION AND PHARMACEUTICAL COMPOSITIONS THEREOF

This application is a 371 of International Application No. PCT/SE98/02091, filed Nov. 18, 1998.

TECHNICAL FIELD

The present invention relates to novel compounds, and therapeutically acceptable salts thereof, which inhibit exogenously or endogenously stimulated gastric acid secretion and thus can be used in the prevention and treatment of gastrointestinal inflammatory diseases. In further aspects, the invention relates to compounds of the invention for use in therapy; to processes for preparation of such new compounds; to pharmaceutical compositions containing at least one compound of the invention, or a therapeutically acceptable salt thereof, as active ingredient; and to the use of the active compounds in the manufacture of medicaments for the medical use indicated above.

BACKGROUND ART

Substituted imidazo[1,2-a]pyrazines are disclosed in EP-A-0068378, U.S. Pat. No. 4,507,294 and EP-A-0204285. Pyrrolo[2,3-d]pyridazines are disclosed in WO 91/17164, WO 92/06979, WO 93/08190 and WO 95/19980. Pyrrolo[1,2-a]pyrazines are disclosed in U.S. Pat. No. 5,041,442.

Benzimidazole and imidazo pyridine derivatives, in which the phenyl moiety is substituted with lower alkyl in 2- and 6-position, and which are effective as inhibitors of the gastrointestinal H$^+$, K$^+$-ATPase, are disclosed in the International Patent Application PCT/SE97/00991 (filing date: Jun. 5, 1997) and in the Swedish Patent Application No. 9700661-3 (filing date: Feb. 25, 1997), respectively.

For a review of the pharmacology of the gastric acid pump (the H$^+$, K$^+$-ATPase), see Sachs et al. (1995) Annu. Rev. Pharmacol. Toxicol. 35: 277–305.

DISCLOSURE OF THE INVENTION

It has surprisingly been found that compounds of the Formula I, which are substituted heterocyclic compounds in which the phenyl moiety is substituted with lower (C$_1$–C$_6$) alkyl in 2- and 6-position, are particularly effective as inhibitors of the gastrointestinal H$^+$, K$^+$-ATPase and thereby as inhibitors of gastric acid secretion.

In one aspect, the invention thus relates to compounds of the general Formula I:

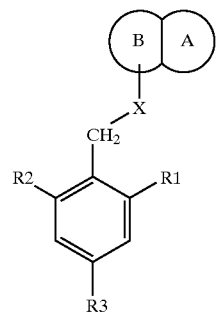

I wherein

R$^1$ is C$_1$–C$_6$ alkyl;

R$^2$ is C$_1$–C$_6$ alkyl;

R$^3$ is H or halogen; and

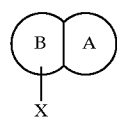

is a substituted heterocycle selected from

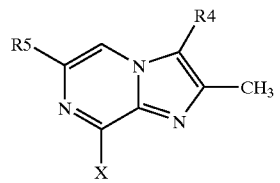

(imidazo[1,2-a]pyrazine)

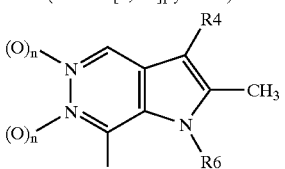

(pyrrolo[2,3-d]pyridazine)

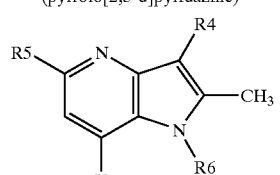

(pyrrolo[2,3-b]pyridine)

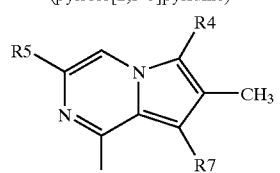

(pyrrolo[1,2-a]pyrazine)

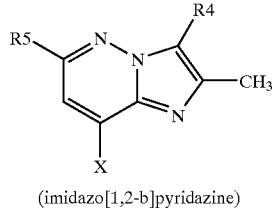

(imidazo[1,2-b]pyridazine)

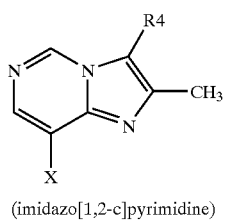

(imidazo[1,2-c]pyrimidine)

wherein

R⁴ is H, CH₃, CH₂OH or CH₂CN;

R⁵ is H or $C_1$–$C_6$ alkyl;

R⁶ is H, $C_1$–$C_6$ alkyl, aryl, arylalkyl containing 1–2 carbon atoms in the alkyl part, $C_2$–$C_6$ alkenyl, halo($C_2$–$C_6$ alkenyl), $C_2$–$C_6$ alkynyl, $C_3$–$C_7$ cycloalkyl or halo($C_1$–$C_6$ alkyl);

R⁷ is H, halogen, $C_1$–$C_6$ alkyl, $C_1$–$C_6$ alkylthio or thiocyano;

n is 0 or 1; and

X is NH or O.

Preferred compounds according to the invention are those wherein:

R¹ is CH₃ or CH₂CH₃;

R² is CH₃ or CH₂CH₃; and

R³ is H, Br, Cl or F.

Other preferred compounds according to the invention are:

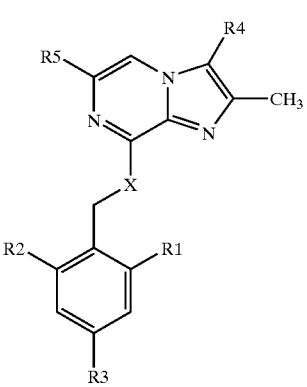

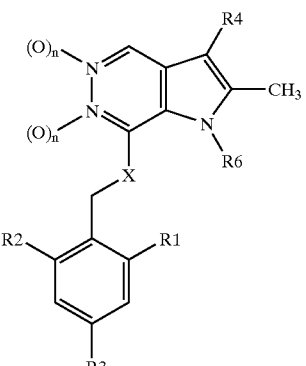

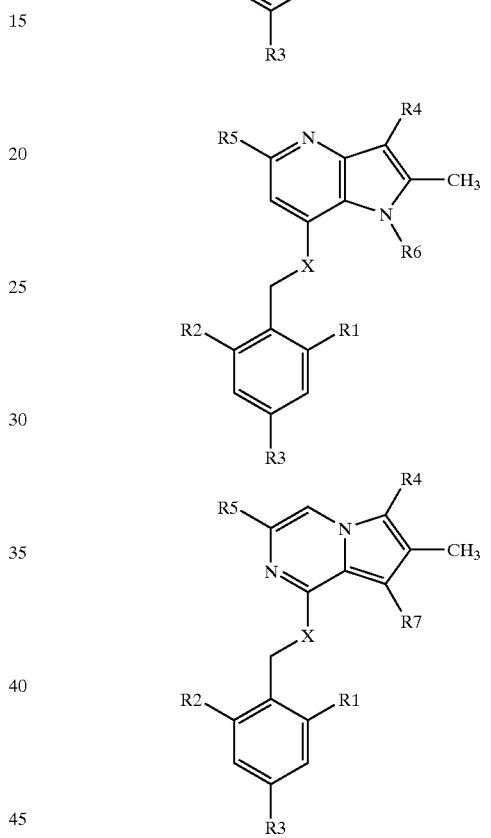

wherein

R⁴ is CH₃ or CH₂OH; and

X, n, R¹, R², R³, R⁵, R⁶ and R⁷ are as defined for Formula I. Particularly preferred are those compounds wherein R¹, R² and R³ are the preferred substituents defined above.

As used herein, the term "$C_1$–$C_6$ alkyl" denotes a straight or branched alkyl group having from 1 to 6 carbon atoms. Examples of said lower alkyl include methyl, ethyl, n-propyl, iso-propyl, n-butyl, iso-butyl, sec-butyl, t-butyl and straight- and branched-chain pentyl and hexyl.

The term "halogen" includes fluoro, chloro, bromo and iodo.

Both the pure enantiomers, racemic mixtures and unequal mixtures of two enantiomers are within the scope of the invention. It should be understood that all the diastereomeric forms possible (pure enantiomers, racemic mixtures and unequal mixtures of two enantiomers) are within the scope of the invention. Also included in the invention are derivatives of the compounds of the Formula I which have the biological function of the compounds of the Formula I.

Depending on the process conditions the end products of the Formula I are obtained either in neutral or salt form. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitably therapeutically acceptable salts. Examples of such acids are hydrohalogen acids such as hydrochloric acid, sulphuric acid, phosphoric acid, nitric acid, aliphatic, alicyclic, aromatic or heterocyclic carboxyl or sulphonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulfonic acid, ethanesulfonic acid, hydroxyethanesulfonic acid, halogenbensenesulfonic acid, toluenesulfonic acid or naphthalenesulfonic acid.

Preparation

The present invention also provides the following processes A and B for the manufacture of compounds with the general Formula I.

Process A

Process A for manufacture of compounds with the general Formula I comprises the following steps:
Compounds of the general Formula II

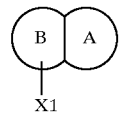

II wherein $X^1$ is OH or $NH_2$, can be reacted with compounds of the general Formula III

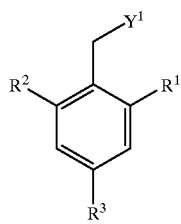

III wherein $R^1$, $R^3$ and $R^4$ are as defined for Formula I and $Y^1$ is a leaving group, such as a halide, tosyloxy or mesyloxy, to the compounds of the Formula I.

It is convenient to conduct this reaction in an inert solvent, e.g. acetone, acetonitrile, dimethoxyethane, methanol, ethanol, xylene or dimethylformamide with or without a base.

The base is e.g. an alkali metal hydroxide, such as sodium hydroxide and potassium hydroxide; a sodium alcoholate, such as sodium methoxide and sodium ethoxide; an alkali metal hydride such as sodium hydride and potassium hydride; an alkali metal carbonate, such as potassium carbonate and sodium carbonate; or an organic amine, such as triethylamine.

Process B

Process B for manufacture of compounds with the general Formula I comprises the following steps:
Compounds of the general Formula IV

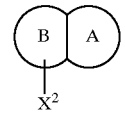

IV wherein $X^2$ is a leaving group e.g. halide, can be reacted with compounds of the general Formula V

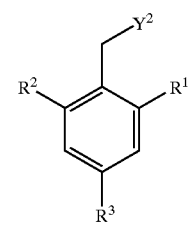

V wherein $R^1$, $R^3$ and $R^4$ are as defined for Formula I and $Y^2$ is $NH_2$ or OH to compounds of the general Formula I.

It is convenient to conduct this reaction in an inert solvent, e.g. acetone, acetonitrile, dimethoxyethane, methanol, ethanol, xylene or dimethylformamide with or without a base. The base is e.g. an alkali metal hydroxide, such as sodium hydroxide and potassium hydroxide; a sodium alcoholate, such as sodium methoxide and sodium ethoxide; an alkali metal hydride such as sodium hydride and potassium hydride; an alkali metal carbonate, such as potassium carbonate and sodium carbonate; or an organic amine, such as triethylamine.

Pharmaceutical Formulations

In yet a further aspect, the invention relates to pharmaceutical compositions containing at least one compound of the invention, or a therapeutically acceptable salt thereof, as active ingredient.

The compounds of the invention can also be used in formulations together with other active ingredients, e.g. antibiotics such as amoxicillin.

For clinical use, the compounds of the invention are formulated into pharmaceutical formulations for oral, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation, preferably between 0.1–20% by weight in preparations for parenteral use and preferably between 0.1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.1% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials.

Solutions for parenteral administration may also be prepared as a dry preparation to by reconstituted with a suitable solvent extemporaneously before use.

The typical daily dose of the active substance varies within a wide range and will depend on various factors such as for example the individual requirement of each patient, the route of administration and the disease. In general, oral and parenteral dosages will be in the range of 5 to 1000 mg per day of active substance.

The compounds according to the invention can also be used in formulations together with other active ingredients, e.g. for the treatment or prophylaxis of conditions involving infection by *Helicobacter pylori* of human gastric mucosa. Such other active ingredients may be antimicrobial agents, in particular:

b-lactam antibiotics such as amoxicillin, ampicillin, cephalothin, cefaclor or cefixime;

macrolides such as erythromycin, or clarithromycin;

tetracyclines such as tetracycline or doxycycline;

aminoglycosides such as gentamycin, kanamycin or amikacin;

quinolones such as norfloxacin, ciprofloxacin or enoxacin;

others such as metronidazole, nitrofurantoin or chloramphenicol; or preparations containing bismuth salts such as bismuth subcitrate, bismuth subsalicylate, bismuth subcarbonate, bismuth subnitrate or bismuth subgallate.

EXAMPLES

Example 1.1

Synthesis of 2,3-dimethyl-8-(2,6-dimethylbenzylamino)imidazo [1,2-a]pyrazine

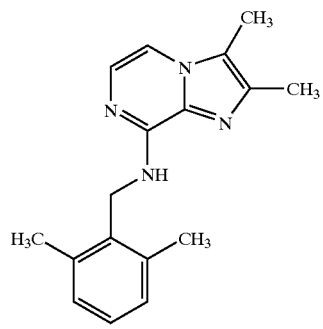

A stirred mixture of 8-chloro-2,3-dimethylimidazo[1,2-a]pyrazine (0.5 g, 2.8 mmol) and 2,6-dimethylbenzylamino (0.41 g, 3.0 mmol) in xylene (10 ml) was refluxed for 24 h.The mixture was evaporated under reduced pressure, dissolved in methylene chloride (20 ml) and was washed with a solution of 5% sodium carbonate in water (20 ml). The organic layer was separated and evaporated under reduced pressure and the residue was purified by column chromatography on silica gel. Crystallization from pentane gave 90 mg (23%) of the title compound.

$^1$H-NMR (300 MHz, CDCl$_3$): δ2.35 (s, 6H), 2.45 (s, 6H), 4.70(d, 2H), 5.60 (bs, 1H), 7.05–7.20 (m, 3H), 7.25 (d, 1H), 7.40 (d, 1H)

Example 1.2

Synthesis of 2,3-dimethyl-8-(2,6-dimethylbenzyloxy)imidazo[1,2-a]pyrazine

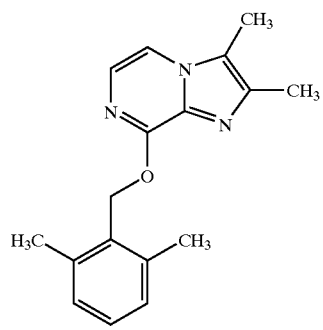

Sodium hydride (0.15 g, 3 mmol) (50% in oil) was added to a stirred solution of 2,6-dimethylbenzylalcohol in acetonitril (10 ml). 8-chloro-2,3-dimethylimidazo[1,2-a]pyrazine (0.4 g, 3 mmol) was added and the reaction mixture was refluxed for 20 h. The solvent was evaporated under reduced pressure and the residue was solved in methylene chloride and washed with water. The organic layer was evaporated under reduced pressure and the residue was purified by column chromatography on silica gel using ethylacetate:petroleum ether(40–60) 1:1 as eluent. Crystallization from petroleum ether gave 0.42 g (50%) of the title compound.

$^1$H-NMR (300 MHz, CDCl$_3$): δ2.35 (s,3H), 2.40 (s, 3H), 2.45 (s, 6H), 5.6 (s, 2H) 6.95–7.15 (m, 3H), 7.35–7.45 (m 2H)

Biological Tests
1. In vitro Experiments
Acid Secretion Inhibition in Isolated Rabbit Gastric Glands Inhibiting effect on acid secretion in vitro in isolated rabbit gastric glands was measured as described by Berglindh et al. (1976) Acta Physiol. Scand. 97, 401–414.

Determination of $H^+,K^+$-ATPase Activity

Membrane vesicles (2.5 to 5 $\mu$g) were incubated for 15 min at +37° C. in 18 mM Pipes/Tris buffer pH 7.4 containing 2 mM $MgCl_2$, 10 mM KCl and 2 mM ATP. The ATPase activity was estimated as release of inorganic phosphate from ATP, as described by LeBel et al. (1978) Anal. Biochem. 85, 86–89.

The compound of Example 1 had an $IC_{50}$ value of 0.16 $\mu$M and the compound of Example 2 had an $IC_{50}$ value of 2.78 $\mu$M.

2. In vivo Experiments
Inhibiting Effect on Acid Secretion in Female Rats

Female rats of the Sprague-Dawly strain are used. They are equipped with cannulated fistulae in the stomach (lumen) and the upper part of the duodenum, for collection of gastric secretions and administration of test substances, respectively. A recovery period of 14 days after surgery is allowed before testing commenced.

Before secretory tests, the animals are deprived of food but not water for 20 h. The stomach is repeatedly washed through the gastric cannula with tap water (+37° C.), and 6 ml Ringer-Glucose given subcutaneously. Acid secretion is stimulated with infusion during 2.5–4 h (1.2 ml/h, subcutaneously) of pentagastrin and carbachol (20 and 110 nmol/kg·h, respectively), during which time gastric secretions are collected in 30-min fractions. Test substances or vehicle are given either at 60 min after starting the stimulation (intravenous and intraduodenal dosing, 1 ml/kg), or 2 h before starting the stimulation (oral dosing, 5 ml/kg, gastric cannula closed). The time interval between dosing and stimulation may be increased in order to study the duration of action. Gastric juice samples are titrated to pH 7.0 with NaOH, 0.1 M, and acid output calculated as the product of titrant volume and concentration.

Further calculations are based on group mean responses from 4–6 rats. In the case of administration during stimulation; the acid output during the periods after administration of test substance or vehicle are expressed as fractional responses, setting the acid output in the 30-min period preceding administration to 1.0. Percentage inhibition is calculated from the fractional responses elicited by test compound and vehicle. In the case of administration before stimulation; percentage inhibition is calculated directly from acid output recorded after test compound and vehicle.

Bioavailability in Rat

Adult rats of the Sprague-Dawley strain are used. One to three days prior to the experiments all rats are prepared by cannulation of the left carotid artery under anaesthesia. The rats used for intravenous experiments are also cannulated in the jugular vein (Popovic (1960) J. Appl. Physiol. 15, 727–728). The cannulas are exteriorized at the nape of the neck.

Blood samples (0.1–0.4 g) are drawn repeatedly from the carotid artery at intervals up to 5.5 hours after given dose. The samples are frozen until analysis of the test compound.

Bioavailability is assessed by calculating the quotient between the area under blood/plasma concentration (AUC) curve following (i) intraduodenal (i.d.) or oral (p.o.) administration and (ii) intravenous (i.v.) administration from the rat or the dog, respectively.

The area under the blood concentration vs. time curve, AUC, is determined by the log/linear trapezoidal rule and extrapolated to infinity by dividing the last determined blood concentration by the elimination rate constant in the terminal phase. The systemic bioavailability (F%) following intraduodenal or oral administration is calculated as F(%)= (AUC (p.o. or i.d.)/AUC (i.v.) )×100.

Inhibition of Gastric Acid Secretion and Bioavailability in the Conscious Dog

Labrador retriever or Harrier dogs of either sex are used. They are equipped with a duodenal fistula for the administration of test compounds or vehicle and a cannulated gastric fistula or a Heidenhaim-pouch for the collection of gastric secretion.

Before secretory tests the animals are fasted for about 18 h but water is freely allowed. Gastric acid secretion is stimulated for up to 6.5 h infusion of histamine dihydrochloride (12 ml/h) at a dose producing about 80% of the individual maximal secretory response, and gastric juice collected in consecutive 30-min fractions. Test substance or vehicle is given orally, i.d. or i.v., 1 or 1.5 h after starting the histamine infusion, in a volume of 0.5 ml/kg body weight. In the case of oral administration, it should be pointed out that the test compound is administered to the acid secreting main stomach of the Heidenham-pouch dog.

The acidity of the gastric juice samples are determined by titration to pH 7.0, and the acid output calculated. The acid output in the collection periods after administration of test substance or vehicle are expressed as fractional responses, setting the acid output in the fraction preceding administration to 1.0. Percentage inhibition is calculated from fractional responses elicited by test compound and vehicle.

Blood samples for the analysis of test compound concentration in plasma are taken at intervals up to 4 h after dosing. Plasma is separated and frozen within 30 min after collection and later analyzed. The systemic bioavailability (F%) after oral or i.d. administration is calculated as described above in the rat model.

What is claimed is:

1. A compound of the formula I

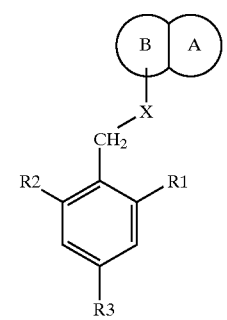

or a pharmaceutically acceptable salt thereof, wherein $R^1$ is $C_1$–$C_6$ alkyl;
$R^2$ is $C_1$–$C_6$ alkyl;
$R^3$ is H or halogen; and

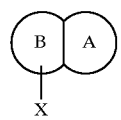

is a substituted heterocycle selected from

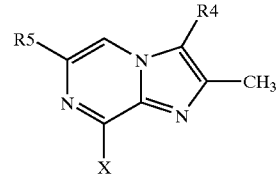

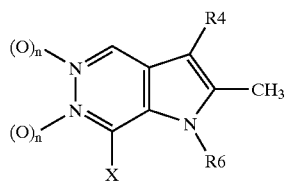

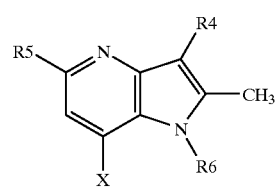

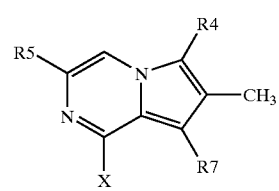

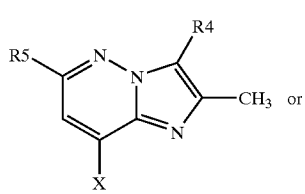

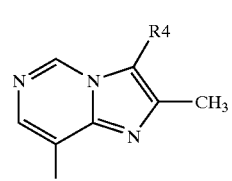

wherein
$R^4$ is H, $CH_3$, $CH_2OH$ or $CH_2CN$;
$R^5$ is H or $C_1$–$C_6$ alkyl;
$R^6$ is H, $C_1$–$C_6$ alkyl, aryl, arylalkyl containing 1–2 carbon atoms in the alkyl part, $C_2$–$C_6$ alkenyl, halo($C_2$–$C_6$ alkenyl), $C_2$–$C_6$ alkynyl, $C_3$–$C_7$ cycloalkyl or halo($C_1$–$C_6$ alkyl);
$R^7$ is H, halogen, $C_1$–$C_6$ alkyl, $C_1$–$C_6$ alkylthio or thiocyano;
n is 0 or 1; and
X is NH or O.

2. A compound according to claim 1, or a pharmaceutically acceptable salt thereof, wherein

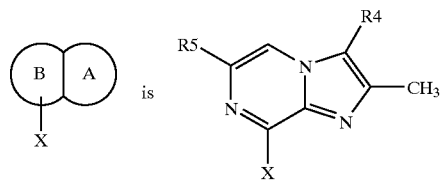

wherein $R^4$, $R^5$ and X are as defined in claim 1.

3. A compound according to claim 1, or a pharmaceutically acceptable salt thereof, wherein

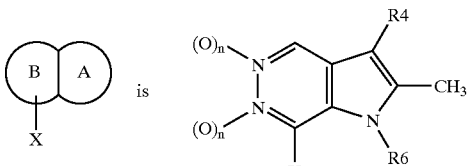

wherein $R^4$, $R^6$ and X are as defined in claim 1.

4. A compound according to claim 1, or a pharmaceutically acceptable salt thereof, wherein

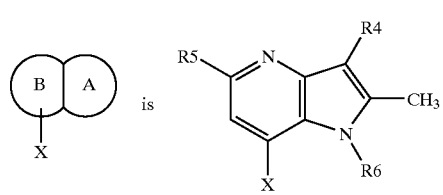

wherein $R^4$, $R^5$, $R^6$ and X are as defined in claim 1.

5. A compound according to claim 1, or a pharmaceutically acceptable salt thereof, wherein

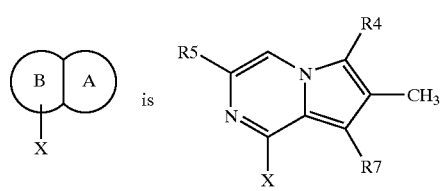

wherein $R^4$, $R^5$, $R^7$ and X are as defined in claim 1.

6. A compound according to claim 1, or a pharmaceutically acceptable salt thereof, wherein

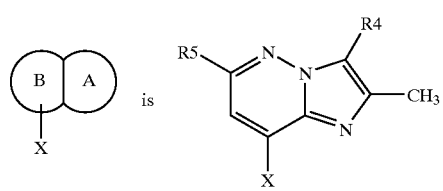

wherein $R^4$, $R^5$ and X are as defined in claim 1.

7. A compound according to claim 1, or a pharmaceutically acceptable salt thereof, wherein

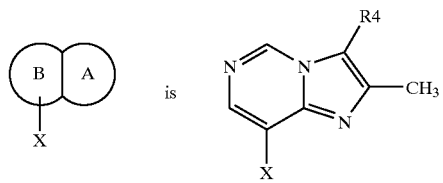

wherein R⁴ and X are as defined in claim 1.

8. A compound according to claim 1, or a pharmaceutically acceptable salt thereof, wherein $R^1$ and $R^2$ are independently $CH_3$ or $CH_2CH_3$.

9. A compound according to claim 2 which is the compound 2,3-dimethyl-8-(2,6-dimethylbenzylamino)imidazo[1,2-a]pyrazine

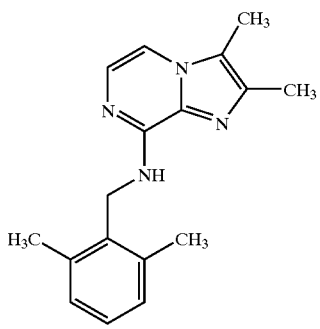

or a pharmaceutically acceptable salt thereof.

10. The compound according to claim 2 which is the compound 2,3-dimethyl-8-(2,6-dimethylbenzyloxy)imidazo[1,2-a]pyrazine

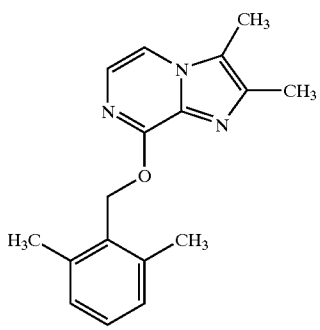

or a pharmaceutically acceptable salt thereof.

11. A process for the preparation of a compound according to any one of claims 1 to 10, comprising reacting a compounds of the general Formula II

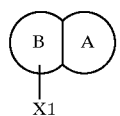

wherein $X^1$ is OH or $NH_2$, with a compound of the general Formula III

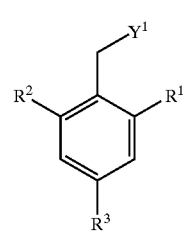

wherein $R^1$, $R^3$ and $R^4$ are as defined for Formula I and $Y^1$ is a leaving group.

12. A process for the preparation of a compound according to any one of claims 1 to 10, comprising reacting a compounds of the general Formula IV

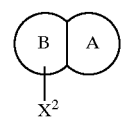

wherein $X^2$ is a leaving group, with a compound of the general Formula V

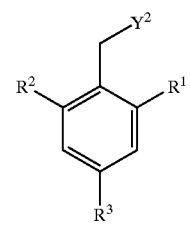

wherein $R^1$, $R^3$ and $R^4$ are as defined for Formula I, and $Y^2$ is $NH_2$ or OH.

13. A pharmaceutical formulation comprising a compound according to any one of claims 1 to 10 as active ingredient in combination with a pharmaceutically acceptable diluent or carrier.

14. A method for inhibiting gastric acid secretion comprising administering to a patient in need of such inhibition an effective amount of a compound according to any one of claims 1 to 10.

15. A method for the treatment of gastrointestinal inflammatory diseases comprising administering to a patient in need of such treatment an effective amount of a compound according to any one of claims 1 to 10.

16. A method for the treatment or prophylaxis of conditions involving infection by *Helicobacter pylori* of human gastric mucosa, comprising administering to a patient in need of such treatment an effective amount of a compound as claimed in any one of claims 1 to 10, in combination with at least one antimicrobial agent.

17. A pharmaceutical formulation for use in the inhibition of gastric acid secretion comprising as active ingredient a compound according to any one of claims 1 to 10 in combination with a pharmaceutically acceptable diluent or carrier.

18. A pharmaceutical formulation for use in the treatment of gastrointestinal inflammatory diseases comprising a compound according to any one of claims 1 to 10 as active ingredient in combination with a pharmaceutically acceptable diluent or carrier.

19. A pharmaceutical formulation for use in the treatment or prophylaxis of conditions involving infection by *Helicobacter pylori* of human gastric mucosa, comprising as active ingredient a compound according to any one of claims 1 to 10 in combination with at least one antimicrobial agent and a pharmaceutically acceptable diluent or carrier.

* * * * *

UNITED STATES PATENT AND TRADEMARK OFFICE
CERTIFICATE OF CORRECTION

PATENT NO.    : 6,518,270 B1
DATED         : February 11, 2003
INVENTOR(S)   : Amin et al.

It is certified that error appears in the above-identified patent and that said Letters Patent is hereby corrected as shown below:

Title page,
Item [75], Inventors, "Starke's" address should be -- Göteborg --.
Item [56], References Cited, FOREIGN PATENT DOCUMENTS, publication date of "WO 9117164" should be -- 11/91 --.
OTHER PUBLICATIONS, "ATPace$^{1,2}$" should be -- ATPase$^{1,2}$ --; and add as a new document:
-- Kaminski et al., "Antiulcer Agents. 6. Analysis of the in Vitro Biochemical and in Vivo Gastric Antisecretory Activity...", J.Med.Chem. 40, 427-436 (1997). --

Column 11,
Lines 1-50, delete the structure numerals in the right margin of the column.

Signed and Sealed this

Twenty-third Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,518,270 B1
DATED         : February 11, 2003
INVENTOR(S)   : Amin et al.

It is certified that error appears in the above-identified patent and that said Letters Patent is hereby corrected as shown below:

Title page,
Item [75], Inventors, "Starke's" address should be -- Göteborg --.
Item [56], References Cited, FOREIGN PATENT DOCUMENTS, publication date of "WO 9117164" should be -- 11/91 --.
OTHER PUBLICATIONS, "ATPace[1,2]" should be -- ATPase[1,2] --; and add as a new document:
-- Kaminski et al., "Antiulcer Agents. 6. Analysis of the in Vitro Biochemical and in Vivo Gastric Antisecretory Activity...", J.Med.Chem. 40, 427-436 (1997). --

Column 11,
Lines 1-50, delete the structure numerals in the right margin of the column.

Signed and Sealed this

Twenty-first Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,518,270 B1  
DATED : February 11, 2003  
INVENTOR(S) : Amin et al.

It is certified that error appears in the above-identified patent and that said Letters Patent is hereby corrected as shown below:

<u>Title page,</u>  
Item [86], the § 371 (c) date should read as:  
-- Dec. 8, 1998 --.

Signed and Sealed this

Seventeenth Day of February, 2004

JON W. DUDAS  
*Acting Director of the United States Patent and Trademark Office*